US012767968B2

(12) United States Patent
Wang et al.

(10) Patent No.: US 12,767,968 B2
(45) Date of Patent: Oct. 20, 2026

(54) **PRODUCTION OF MELANIN IN *VIBRIO NATRIEGENS***

(71) Applicant: The Government of the United States of America, as represented by the Secretary of the Navy, Arlington, VA (US)

(72) Inventors: Zheng Wang, Burke, VA (US); Aaron Smith, Alexandria, VA (US); Tanya Tschirhart, Odenton, MD (US); Jaimee Compton, Washington, DC (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 442 days.

(21) Appl. No.: 18/229,933

(22) Filed: Aug. 3, 2023

(65) Prior Publication Data

US 2024/0060105 A1 Feb. 22, 2024

Related U.S. Application Data

(60) Provisional application No. 63/398,555, filed on Aug. 17, 2022.

(51) Int. Cl.

| | |
|---|---|
| ***C12P 17/18*** | (2006.01) |
| ***C12N 1/20*** | (2026.01) |
| ***C12N 9/02*** | (2006.01) |
| ***C12N 15/74*** | (2006.01) |
| ***C12R 1/63*** | (2006.01) |

(52) U.S. Cl.

CPC .............. *C12P 17/182* (2013.01); *C12N 1/20* (2013.01); *C12N 9/0071* (2013.01); *C12N 15/74* (2013.01); *C12N 2500/32* (2013.01); *C12N 2523/00* (2013.01); *C12R 2001/63* (2021.05); *C12Y 114/18001* (2013.01)

(58) Field of Classification Search

CPC ....... C12P 17/182; C12N 1/20; C12N 9/0071; C12N 15/74; C12N 2500/32; C12N 2523/00; C12R 2001/63; C12Y 114/18001

See application file for complete search history.

(56) References Cited

U.S. PATENT DOCUMENTS 5,631,151 A * 5/1997 della-Cioppa ............................... C12Y 110/03001 435/189
11,162,212 B2 * 11/2021 Wang .................... D06P 1/0052
2011/0151496 A1 6/2011 Stephanopoulos
2020/0024797 A1 1/2020 Wang et al.

OTHER PUBLICATIONS

"L-Tyrosine Disodium Salt Dihydrate" (Product Page and Information, Millipore Sigma product # 137254, available at www.sigmaaldrich.com/US/en/product/sigma/137254). Accessed on Sep. 25, 2025 (Year: 2025).*

Vercruysse et al., "Melanogenesis using tyrosinate (not tyrosinase)", ChemRxiv, Aug. 7, 2018 (Posted date), Doi: 10.26434/chemrxiv.6936653.vl, pp. 1-25. (Year: 2018).*

Wang et al., "Melanin Produced by the Fast-Growing Marine Bacterium Vibrio natriegens through Heterologous Biosynthesis: Characterization and Application," Applied and Environmental Microbiology, 2020, 86 (5), e02749-19. DOI: 10.1128/AEM.02749-19 (Year: 2020).*

"Shanghai_SFLS_SPBS: Not hair die, hair DYE (2020)—Team Presentation [English]", iGEM Video Universe, accessed at //video.igem.org/w/mwecojrvRzSXr2KJikaG8D; a print out of the webpage including the Abstract is provided with this communication, 3 pages total (Year: 2020).*

Smith et al. 2023, "Rapid, high-titer biosynthesis of melanin using the marine bacterium Vibrionatriegens". Front. Bioeng. Biotechnol. 11:1239756. doi: 10.3389/fbioe.2023.1239756. (Year: 2023).*

Wang et al., "Melanin Produced by the Fast-Growing Marine Bacterium Vibrio natriegens through Heterologous Biosynthesis: Characterization and Application," Applied and Environmental Microbiology, 2020, 86 (5), e02749-19. DOI: 10.1128/AEM.02749-19.

B. Choi, "Bioprocess of Microbial Melanin Production and Isolation," Front. Bioeng. Biotechnol., 2021, DOI: 10.3389/fbioe.2021.765110.

International Search Report mailed Nov. 16, 2023 in PCT/US2023/029399.

Written Opinion of the International Searching Authority mailed Nov. 16, 2023 in PCT/US2023/029399.

Babu, Badisa Ramesh et al., "Effect of an abundant human skin melanosomal 66 kDa protein (MP 66) on murine tyrosinase: Its physiological implications on melanogenesis", Journal of Biosciences, Jun. 1998, vol. 23, No. 2, pp. 125-129.

Vercruysse, Koen P. et al., "Melanogenesis using tyrosinate (not tyrosinase)", ChemRxiv, Aug. 7, 2018 (Posted date), Doi: 10.26434/chemrxiv.6936653.vl, pp. 1-25.

* cited by examiner

*Primary Examiner* — Anand U Desai
*Assistant Examiner* — Andrew T Moehlman
(74) *Attorney, Agent, or Firm* — US Naval Research Laboratory; Fariborz Moazzam

(57) ABSTRACT

Improved yields of melanin are obtained by incubating, in an optimized media with a disodium tyrosine substrate, a culture of *Vibrio natriegens* expressing a heterologous tyrosinase gene at a temperature of about 30° C.

3 Claims, 2 Drawing Sheets

| Iteration | 1 | 2 | 3 | 4 | 5 | 6* |
|---|---|---|---|---|---|---|
| Species | *E. coli* | *V. natriegens* | *V. natriegens* | *V. natriegens* | *V. natriegens* | *V. natriegens* |
| Media | LB | LB | VnM9v2 | VnM9v2 | VnM9v2 | VnM9v3 |
| Temperature | 37°C | 37°C | 37°C | 37°C | 30°C | 30°C |
| Substrate | Tyrosine | Tyrosine | Tyrosine | Disodium Tyrosine | Disodium Tyrosine | Disodium Tyrosine |
| Yield | ~0.5 g/L | 1 g/L | 2 g/L | 4 g/L | 8 g/L | 7 g/L |

FIG. 1

| No | Sources | Melanin type | Host strain | Genes expressed | Substrate (conc.) | Reaction condition | Reaction time | Production |
|---|---|---|---|---|---|---|---|---|
| 1 | Plant | — | *Mucuna monosperma (Wight) callus* | — | Tyrosine (1 g/L) | pH 5.5 | 48 h | 0.687 g/L |
| 2 | Fungus | — | *Auricularia auricula* | Wild type | Tyrosine (1.92 g/L), yeast extract (17.27 g/L), lactose (3.84 g/L) | pH 6, 28°C | 8 days | 2.97 g/L |
| 3 | Fungus | Eumelanin | *Gliocephalotrichum simplex* | Wild type | Tyrosine (2.5% w/v), peptone (1% w/v) | 28°C | 6 days | 6.6 g/L |
| 4 | Fungus | Eumelanin | *Armillaria cepistipes* | Wild type | Tyrosine (3.0% w/v) | pH 6, 22°C | 161 days | 27.98 g/L |
| 5 | Bacterial | Eumelanin | *Klebsiella sp. GSK 46* | Wild type | Tyrosine (1 g/L) | pH 7.2, 37°C | 3.5 days | 0.13 g/L |
| 6 | Bacterial | Eumelanin | *Pseudomonas stutzeri* | Wild type | Sea-water medium without tyrosine | pH 6.7, 37°C | 10 h | 6.7 g/L |
| 7 | Bacterial | Eumelanin | *Streptomyces kathirae* | Wild type | Amylodextrine (3.3 g/L), yeast extract (5 g/L) | pH 6, 28°C | 128 h | 13.7 g/L |
| 8 | Bacterial | Eumelanin | *Bacillus safensis* | Wild type | Fruit waste extract | pH 6.84, 30.7°C | 24 h | 6.96 g/L |
| 9 | Bacterial | Eumelanin | *Streptomyces glaucescens NEAE-H* | Wild type | Protease-peptone (5 g/L) | 30–37°C | 6 days | 3.16 g/L |
| 10 | Bacterial | Eumelanin | *Streptomyces sp. ZL-24* | Wild type | Soy peptone (20.31 g/L) | pH 7, 30°C | 5 days | 4.24 g/L (189.9 mg/L insoluble) |
| 11 | Bacterial | Eumelanin | *Bacillus subtilis 4NP-BL* | Wild type | Starch (15 g/L) | pH 7.2, 28°C | 7 days | 1.5 g/L |
| 12 | Bacterial | Eumelanin | *Escherichia coli* | *melC, cyp102G4* | Tyrosine, indole | pH 7, 37°C | 24 h | 3.4 g/L |
| 13 | Bacterial | Eumelanin | *Pseudomonas koreensis UIS 19* | Wild type | Molasses 5 Brix (5%), tyrosine (2.5 g/L) | pH 7.5, 30°C | 24 h | 5.5 g/L |
| 14 | Bacterial | Eumelanin | *Amorphotheca resinae* | Wild type | Peptone (10 g/L), yeast extract (5 g/L), glucose (20 g/L) | 27°C | 14 days | 4.5 g/L (13.4 mg/L/h) |
| 15 | Marine Bacterium | Eumelanin | *Vibrio natriegens* | *tyr1* | Tyrosine (0.4 g/L) | 30°C | 2 h | 0.45 g/L (0.32 mg/mL/h) |
| 16 | Bacterial | Pyomelanin | *Escherichia coli* | *4-hppd* | Tyrosine (1 mM) | pH 7, 37°C | 6 days | 0.213 g/L |
| 17 | Bacterial | Pyomelanin | *Ralstonia picketti* | Wild type | Tyrosine (4 mM) | pH 7, 30°C | 62 h | 0.09 g/L |
| 18 | Bacterial | Pyomelanin | *Escherichia coli* | *4-hppd* | Tyrosine (4 mM) | pH 7, 30°C | 24 h | 0.315 g/L (13.1 mg/L/h) |
| 19 | Bacterial | Pyomelanin | *Yarrowia lypolytica* W29 | 4-HPPD | Tyrosine (1 g/L) | pH 7, 37°C | 72 h | 0.5 g/L |
| 20 | Bacterial | Allomelanin | *Escherichia coli* | *fcs/ech* | Caffeic acid (5 mM) | pH 7, 37°C | 12 h | 0.2 g/L (40.9 mg/L/h) |
| 21 | Bacterial | Allomelanin | *Escherichia coli* | *fcs/ech* | Caffeic acid (0.5 mM) | pH 7, 37°C | 12 h | 0.17 g/L (14.2 mg/L/h) |

FIG. 2
PRIOR ART

PRODUCTION OF MELANIN IN *VIBRIO NATRIEGENS*

CROSS-REFERENCE TO RELATED APPLICATIONS

This application claims the benefit of U.S. Provisional Patent Application No. 63/398,555 filed on Aug. 17, 2023, the entirety of which is incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, DC 20375, USA; +1.202.767.7230; techtran@nrl.navy.mil, referencing NC 211,155.

BACKGROUND

Melanins are macromolecules formed by oxidative polymerization of phenolic and/or indolic compounds. These black or brown pigments are hydrophobic, negatively charged, and ubiquitous in nature and impart a large variety of biological functions to organisms, including structure, coloration, free radical scavenging, radiation resistance, and thermoregulation. Inspired by the physicochemical, optoelectronic, self-assembling, and adhesive properties of natural melanin, a number of research groups have synthesized melanin nanoparticles for a broad range of applications, including protective coatings, functional films, environmental sensors, and energy storage devices. For example, melanin can be used in chemical protective materials, such as garments, as described in commonly-owned U.S. Pat. No. 11,162,212.

A process for production of melanin was described in Wang et al., "Melanin Produced by the Fast-Growing Marine Bacterium *Vibrio natriegens* through Heterologous Biosynthesis: Characterization and Application," *Applied and Environmental Microbiology,* 2020, 86 (5), e02749-19 (hereinafter, "Wang et al.", incorporated herein by reference for the purposes of disclosing techniques for obtaining melanin from cultures of *Vibrio*). Under the conditions described therein, melanin with yield were approximately 1 g per liter.

A need exists for improved yields in the production of melanin from *Vibrio natriegens.*

BRIEF SUMMARY

In one embodiment, a method for producing melanin comprises incubating a culture of *Vibrio natriegens* expressing a tyrosinase gene in a liquid media comprising disodium tyrosine at a temperature greater than 25° C. and less than 37° C., and obtaining melanin from the culture. Optionally, the tyrosinase from *Bacillus megaterium* is expressed under the control of an inducible promoter.

In a further embodiment, the temperature is between 26° C. and about 35° C. In a still further embodiment, the temperature is 30° C.

In additional embodiments, the liquid media is VnM9v2 and the culture is grown in a shaker flask, or the liquid media is M9v3 and the culture is grown in a bioreactor.

BRIEF DESCRIPTION OF THE DRAWINGS

FIG. 1 provides a table showing key developments towards improving melanin production yields. Significant changes include the switch from *E. coli* to *V. natriegens* at iteration 2, the change in media at iteration 3, the use of disodium tyrosine at iteration 4, the reduced temperate at iteration 5, and the further change in media at interation 6 (starred). Approximate respective yields obtained after each iteration is reported at the bottom. For the sixth iteration, a VnM9v3 media was developed that was optimized specifically for culture growth in bioreactors as compared to the VnM9v2 formulation that was optimized for shaker flask cultures.

FIG. 2 shows comparative results of various microbial processes for obtaining melanin, adapted from Choi, "Bioprocess of Microbial Melanin Production and Isolation," *Front. Bioeng. Biotechnol.,* 2021, DOI: 10.3389/fbioe.2021.765110. Here, melC is tyrosinase from *Bacillus megaterium*, cyp102G4 is cytochrome P450 monooxygenase from *Streptomyces cattleya,* 4-hppd is 4-hydroxyphenylpyruvate dioxygenase, and tyr1 is tyrosinase from *Bacillus megaterium.*

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

Compared to the process for obtaining melanin described Wang et al., the approach described herein obtained approximately eight times higher yield. Improvements arose from a combination of changes in growth media, culture temperature, and tyrosine source.

A defined minimal media was developed, optimized for *V. natriegens* growth, focusing on a number of factors including essential elemental sources/concentrations (nitrogen, sulfur, phosphorous), salt concentrations (NaCl), carbon sources and concentrations (such as glucose and glycerol as well as alternative carbon sources (xylose, citrate, lactose, etc.). Also examined were additional supplements (such as casamino acids, buffers, aspartate, thiamine, and metals). This work led to a media formulation termed "VnM9v2."

A comparative analysis was made of enzymes for biosynthesis of melanin, comparing Tyr1 vs HpaBC vs MelA. Tyr1 was found to be the most efficient of these melanin biosynthetic enzymes.

Also examined were various promoters of expression, including constitutive and inducible promoters, the latter including those inducible by IPTG (isopropyl ß-D-1-thio-galactopyranoside), copper, and arabinose. While the IPTG promoter was found to produce the best results, another promoter could be used to avoid the cost of using IPTG.

Regarding substrates, the low solubility of substrate tyrosine in the growth medium (no more than ~0.5 g/L) limited the yield of product melanin. Switching from tyrosine to disodium tyrosine as a substrate increased product yields, as disodium tyrosine has much greater solubility than tyrosine (greater than 100-fold) allowing for addition of much more substrate to increase the product yield.

Additional improvements were had by using an initial growth phase at 37° C. followed by incubation at 30° C. during biosynthesis.

The above-described VnM9v2 media, used for shaker flask cultures, was further refined in what was termed VnM9v3 specifically formulated for optimal growth in bioreactor. This involved two key changes. First was substitution of NaCl with $Na_2SO_4$. Although high sodium ion content is required for optimal *V. natriegens* growth, the high chloride ion content associated with use of NaCl would tend to cause bioreactor corrosion. This substitution mitigates this concern. The second change was a reduction in phosphate content from 100 mM to 20 mM final concentration. This presents a substantial cost savings for large scale production. Additionally, since bioreactors typically have automated pH sensing and control, the higher buffering capacity required to maintain pH in shake flasks cultures (100 mM phosphate) is not required in bioreactors in which a lower buffering capacity is preferred (20 mM phosphate).

The combination of incubation at 30° C. during biosynthesis (instead of 37° C.) and the use of the optimized media surprisingly and unexpectedly resulted in a large increase in the melanin yield (FIG. 1). The resulting bioproduction process has yielded one of the highest yields and productivities currently reported in the literature, while using the convenient *Vibrio natriegens* platform.

EXAMPLES

The stocks used in the *V. natriegens* high density growth minimal media for melanin biosynthesis termed VnM9v2, optimized for use in shaker flask culture, were as follows. All were autoclaved except as noted with an asterisk.

1. 20× Minimal Salts
   - 1.60 M $K_2HPO_4$
   - 0.4 M $NaH_2PO_4$
   - 1 M $NH_4Cl$
   - 0.1 M $Na_2SO_4$
2. 5 M NaCl
3. 1 M $MgSO_4$
4. 100 mM $CaCl_2$
5. 40× Carbon Sources
   - 20% (w/v) Glycerol
   - 20% (w/v) Glucose
6. 10% (w/v) Casamino Acids*
7. 25% (w/v) Aspartate
   - 84 mL water
   - 25 g Aspartic Acid
   - 8 g NaOH
8. 0.1 M $FeCl_3$*
   - Dissolved in 0.1 M HCl
9. 1000× Essential Metals Mix*#
   - 50 mM $FeCl_3$ (from 0.1 M stock in HCl)
   - 10 mM $MnCl_2$
   - 10 mM $ZnSO_4$
   - 2 mM $CoCl_2$
   - 2 mM $CuCl_2$
   - 2 mM $NiCl_2$
   - 2 mM $Na_2MoO_4$
   - 2 mM $Na_2SeO_3$
   - 2 mM $H_3BO_3$
10. 10 mM Thiamine HCl*

* Do not autoclave. Filter sterilize with 0.2 μm filters.

#Make 0.1 M stocks of each element. Only $FeCl_3$ stock is dissolved in 0.1 M HCl From these stocks, the recipe for preparing one liter of VnM9v2 media is as follows:

- 840 mL Autoclaved Water
- 50 mL 20× Minimal Salts
- 1 mL 1 M $MgSO_4$
- 3 mL 100 mM $CaCl_2$
- 20 mL 40× Carbon Sources
- 20 mL 10% (w/v) Casamino Acids
- 8 mL 25% (w/v) Aspartate
- 0.2 mL 1000× Essential Metals Mix
- 0.1 mL 10 mM Thiamine HCl
- An appropriate concentration of selective antibiotic This results in the following final concentrations in the VnM9v2 media ready for use:

- 80 mM $K_2HPO_4$
- 20 mM $NaH_2PO_4$
- 50 mM $NH_4Cl$
- 5 mM $Na_2SO_4$
- 275 mM NaCl
- 1 mM $MgSO_4$
- 0.3 mM $CaCl_2$
- 0.4% (wt/vol) Glycerol
- 0.4% (wt/vol) Glucose
- 0.2% (wt/vol) Casamino Acids
- 0.2% (wt/vol) Aspartate
- 0.2× Essential Trace Metals Mix
- 1 μM Thiamine The optimized process, for cultures in shaker flasks, is as follows:

- Inoculate 1 L of media to a starting $OD_{600}$=0.1 from a starter culture of *V. natriegens* transformed with pJV-Tyr1 (IPTG inducible Tyr1 plasmid)
- Grow culture at 37° C., 200 rpm, until $OD_{600}$~ 0.8 (roughly 2 hours)
- Add IPTG to a final concentration of 1 mM
- Reduce temperature to 30° C. and continue to incubate at 200 rpm for another 3 hours to allow for Tyr1 induction
- After induction period, supplement cultures with 40 μM $CuSO_4$ and 8 mg/mL disodium tyrosine
- Continue incubating cultures at 30° C., 200 rpm, overnight (minimum of 12 hours) for bioproduction of melanin The stocks used in the *V. natriegens* high density growth minimal media for melanin biosynthesis termed VnM9v3, optimized for use in a bioreactor, were as follows. All were autoclaved except as noted with an asterisk.

1. 10× Minimal Salts
   - 160 mM $K_2HPO_4$
   - 40 mM $NaH_2PO_4$
   - 500 mM $NH_4Cl$
   - 1.3 M $Na_2SO_4$
2. 1 M $MgSO_4$
3. 100 mM $CaCl_2$
4. 40× Carbon Sources
   - 20% (w/v) Glycerol
   - 20% (w/v) Glucose
5. 10% (w/v) Casamino Acids*
6. 25% (w/v) Aspartate 84 mL water
25 g Aspartic Acid
8 g NaOH 7. 0.1M $FeCl_3$*
Dissolved in 0.1 M HCl
8. 1000× Essential Metals Mix*#
50 mM FeCl3 (from 0.1 M stock in HCl)
10 mM $MnCl_2$
10 mM $ZnSO_4$
2 mM $CoCl_2$
2 mM $CuCl_2$
2 mM $NiCl_2$
2 mM $Na_2MoO_4$
2 mM $Na_2SeO_3$
2 mM $H_3BO_3$
9. 10 mM Thiamine HCl*

* Do not autoclave. Filter sterilize with 0.2 μm filters.

#Make 0.1 M stocks of each element. Only $FeCl_3$ stock is dissolved in 0.1 M HCl From these stocks, the recipe for preparing one liter of VnM9v3 media is as follows:

845 mL Autoclaved Water
100 mL 10× Minimal Salts
1 mL 1 M $MgSO_4$
3 mL 100 mM $CaCl_2$
20 mL 40× Carbon Sources
20 mL 10% (w/v) Casamino Acids
8 mL 25% (w/v) Aspartate
0.2 mL 1000× Essential Metals Mix
0.1 mL 10 mM Thiamine HCl
An appropriate concentration of selective antibiotic This results in the following final concentrations in the VnM9v3 media ready for use:

16 mM $K_2HPO_4$
4 mM $NaH_2PO_4$
50 mM $NH_4Cl$
130 mM $Na_2SO_4$
1 mM $MgSO_4$
0.3 mM $CaCl_2$
0.4% (wt/vol) Glycerol
0.4% (wt/vol) Glucose
0.2% (wt/vol) Casamino Acids
0.2% (wt/vol) Aspartate
0.2× Essential Trace Metals Mix
1 μM Thiamine Melanin production in a bioreactor was accomplished as follows using an Eppendorf DASBOX system (mini bioreactor system for cell culture and microbiology) with additional DASGIP MP8 pump controller module and DASGIP OD4 sensor module. Experimental parameters were all adjusted and set using the accompanying DASware control 5 software.

100 mL filter sterilized VnM9v3+30 μg/ml chloramphenicol was added to autoclaved reactor vessels. Overnight culture of *V. natriegens* transformed with pJV-Tyr1 was added to final $OD_{600}$ of 0.1. Cultivation of cells were carried out a temperature of 37° C. until $OD_{600}$ reached 1.0. Temperature was reduced to 30° C. and IPTG was added to a final concentration of 0.1 mM and incubated for an additional 3 h. After induction period, 40 μM $CuSO_4$ and 8 mg/mL disodium tyrosine were added to reactors.

The reactor parameters were:

Temperature was maintained at 30° C. after induction period (37° C. pre-induction) using a temperature probe.

Dissolved oxygen (DO) was set to 30% and was sensed by an $O_2$ sensor and controlled by an automated cascade consisting of increased impeller speeds and increased air flow:
p-value=0.5
N: 0-40%, 400-1200 rpm
XO2: 40-80%, 21% constant
F: 40-100%, 6-18 sL/h pH set point was set at 7.0 and monitored using a pH probe
Used 1M $H_3PO_4$ and 3M NaOH for automated pH control Level sensor was used for automatic anti-foam injections using stock of 1% propylene glycol 2000 (PPG2000) and a custom level sensor script:
1) If p.LvlPV>400
2) p.FCSP=10
3) Else
4) p.FCSP=0
5) End if

Further Embodiments

In various aspects, the growth media can have a chloride ion concentration in the range of 25-75 mM while maintaining sufficient sodium for *V. natriegens* growth (typically by using a non-chloride salt as a sodium source to reach at least 100 mM sodium). In further aspects, the growth media can have a phosphate ion concentration in the range of 10-30 mM.

CONCLUDING REMARKS

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

1. U.S. Pat. No. 11,162,212.
2. Wang et al., "Melanin Produced by the Fast-Growing Marine Bacterium *Vibrio natriegens* through Heterologous Biosynthesis: Characterization and Application," *Applied and Environmental Microbiology,* 2020, 86 (5), e02749-19. DOI: 10.1128/AEM.02749-19
3. Choi, "Bioprocess of Microbial Melanin Production and Isolation," *Front. Bioeng. Biotechnol.,* 2021, DOI: 10.3389/fbioe.2021.765110

What is claimed is:

1. A method for producing melanin comprising:
incubating in a liquid media a culture of *Vibrio natriegens* expressing a heterologous tyrosinase from *Bacillus megaterium* at a temperature between 26° C. and 35° C., inclusive, and obtaining melanin from the culture
wherein the liquid media comprises disodium tyrosine and the following components: 16 mM $K_2HPO_4$, 4 mM $NaH_2PO_4$, 50 mM $NH_4Cl$, 130 mM $Na_2SO_4$, 1 mM $MgSO_4$, 0.3 mM $CaCl_2$, 0.4% (wt/vol) glycerol, 0.4% (wt/vol) glucose, 0.2% (wt/vol) casamino acids, 0.2% (wt/vol) aspartate, and 1 μM thiamine, wherein each component is initially present in an amount within +/−20% from the listed quantity.

2. The method of claim 1, wherein the temperature is about 30° C.

3. The method of claim 1, further comprising first growing the culture at a temperature of 37° C. prior to inducing expression of said tyrosinase and reducing the temperature to said between 26° C. and 35° C., inclusive.

* * * * *